United States Patent
Bai et al.

(10) Patent No.: US 7,569,827 B2
(45) Date of Patent: Aug. 4, 2009

(54) EMISSION-DATA-BASED PHOTON SCATTER CORRECTION IN COMPUTED NUCLEAR IMAGING TECHNOLOGY

(76) Inventors: Chuanyong Bai, 13120 Grape Arbor Way, Poway, CA (US) 92064; Richard L. Conwell, 13684 Boquita Dr., Del Mar, CA (US) 92014

( * ) Notice: Subject to any disclaimer, the term of this patent is extended or adjusted under 35 U.S.C. 154(b) by 0 days.

(21) Appl. No.: 11/506,152

(22) Filed: Aug. 16, 2006

(65) Prior Publication Data
US 2007/0200066 A1 Aug. 30, 2007

Related U.S. Application Data

(60) Provisional application No. 60/708,833, filed on Aug. 16, 2005.

(51) Int. Cl.
*G01T 1/166* (2006.01)
*G06K 9/00* (2006.01)
(52) U.S. Cl. ............... 250/363.04; 250/363.02; 250/363.07; 250/363.09; 382/131
(58) Field of Classification Search ........... 250/369, 250/363.04, 363.1, 363.07, 370.09; 382/131
See application file for complete search history.

(56) References Cited

U.S. PATENT DOCUMENTS

| | | | | |
|---|---|---|---|---|
| 5,767,517 | A  * | 6/1998 | Hawkins | 250/363.04 |
| 6,175,118 | B1 * | 1/2001 | Takayama et al. | 250/369 |
| 6,177,675 | B1 * | 1/2001 | Gagnon et al. | 250/363.1 |
| 6,194,726 | B1   | 2/2001 | Pi et al. | |
| 7,060,983 | B2 * | 6/2006 | Tumer | 250/370.09 |
| 7,164,130 | B2   | 1/2007 | Welsh et al. | |
| 2002/0020846 | A1 | 2/2002 | Pi et al. | |
| 2005/0189494 | A1* | 9/2005 | Conwell | 250/363.04 |
| 2006/0157653 | A1 | 7/2006 | Conwell | |
| 2006/0173302 | A1 | 8/2006 | Conwell | |
| 2007/0092144 | A1 | 4/2007 | Bai et al. | |
| 2007/0217666 | A1* | 9/2007 | Gal et al. | 382/131 |

OTHER PUBLICATIONS

Bai, et al., "A slice-by-slice blurring model and kernel evaluation using the Klein-Nishina formula for 3D scatter compensation in parallel and converging beam SPECT", May 2000, Phys. Med. Biol., vol. 45, pp. 1275-1307.

* cited by examiner

*Primary Examiner*—David P Porta
*Assistant Examiner*—Casey Bryant
(74) *Attorney, Agent, or Firm*—Law Ofc SC Harris

(57) ABSTRACT

An image from a gamma camera, e.g., from a radiopharmaceutical, is corrected for scatter. The image is approximated by estimating the center of the organ and supposing a Gaussian response that is scatter-corrected.

12 Claims, 5 Drawing Sheets

1. Definition:

$$f(x) * g(x) = \int_{-\infty}^{+\infty} f(x')g(x-x')dx'$$

Example:

$$g(x) = \frac{1}{\sigma\sqrt{2\pi}} e^{-\frac{x^2}{2\sigma^2}}$$

$$f(x) = rect\left(\frac{x}{L}\right)$$

then:

$f(x)*g(x)$ is $f(x)$ "smeared with $g(x)$".

EMISSION-DATA-BASED PHOTON SCATTER CORRECTION IN COMPUTED NUCLEAR IMAGING TECHNOLOGY

CROSS-REFERENCE TO RELATED APPLICATIONS

This application claims priority to U.S. application Ser. No. 60/708,833, filed on Aug. 16, 2005. The disclosure of the prior application is considered part of (and is incorporated by reference in) the disclosure of this application.

BACKGROUND

Medical imaging systems may use nuclear materials, called radiopharmaceuticals, for imaging. First, an organ of interest to be imaged is identified. Then, pharmaceuticals are selected that will preferentially accumulate in that organ of interest. Radioactive tracers are attached to those pharmaceuticals, then administered to the patient. Radioactive tracers collect in the organs, then decay, emitting gamma radiation. Detectors such as gamma cameras are sensitive to gamma radiation to convert the radiation into corresponding electrical pulses.

Gamma cameras may be used in planar imaging. This imaging is also used in single photon emission computed tomography, or SPECT. In SPECT imaging, many projection images may be acquired from different projection angles, which are then used to reconstruct a three-dimensional model of the organ of interest.

One problem in nuclear imaging is photon scatter. Scatter results when waves and particles collide, deflecting waves from their original path. Consequently, waves may differ from their original direction of propagation, energy, and phase. In Compton scattering, the gamma rays collide with electrons in body tissue. The incident photon loses some of its energy, and is deflected from its original path. In medical imaging without scatter correction it is assumed that the detected photons traveled in a direct path from the source of radiation to the detector surface without accounting for the deflections. Therefore, scatter artifacts are left because the deflected photons are restored to the wrong points of origin. Consequently, the reconstructed image contains artifacts that increase the background and reduce contrast.

Image contrast improvement is important in several applications. For example, in planar imaging of tumors, high tumor to background contrast is desired. In SPECT oncology, high tumor to background contrast is critical for tumor detection. In cardiac studies, accurate cardiac wall to chamber contrast is important for accurate ejection fraction quantization. An accurate perfusion image of the myocardium wall is also critical for diagnosis and prognosis. Scatter can significantly reduce the cardiac wall to chamber contrast and can make an under-perfused myocardial wall appear normal.

Techniques have been developed for scatter correction. A first technique models scatter based on data acquired in energy windows outside of the photon peak window. The image is then adjusted to account for the modeled scatter. However, this technique requires acquisition of additional data that increases the complexity of the data acquisition software, the acquisition setup, and also the management of the patient database. Furthermore, the accuracy of the technique is also limited by the accuracy of the model, and the amount of noise acquired in the additional scatter windows.

A second technique estimates the scattered photons based on physics models that model the Compton scatter process. Some techniques use Monte Carlo (or pseudo Monte Carlo) simulation in the iterative reconstruction to estimate photon scatter. The accuracy of these techniques is limited by the accuracy of the physics model and the accuracy of the attenuation maps. Furthermore, the technique can be very computationally expensive.

SUMMARY

An imaging system comprising a data acquisition system that includes a processor for scatter correction. A corrected signal is formed from said system. An embodiment describes a data acquisition system with an imaging head, or gamma-ray detector and an entrance aperture such as a collimator for directing the rays to the detector. The detector may comprise a plurality of closely-packed solid-state detection modules or use a scintillator(s) and photodetectors. The signal processor acquires data from the gamma-ray detector, normalizes and formats the data, and stores it in memory blocks for output.

The data acquisition system captures projections at given increments around a periphery, e.g., 360 degrees or 180 degrees. The processor approximates the scatter from the acquired emission data using the average Gaussian scatter response of the organ of interest and the emission-to-scatter ratio of the organ of interest. The processor then uses that information to reconstruct the image and correct for scatter.

DETAILED DESCRIPTION

The general structure and techniques, and more specific embodiments which can be used to effect different ways of carrying out the more general goals, are described herein.

Data Acquisition

An embodiment administers radiopharmaceuticals to a patient to be imaged. The radiopharmaceuticals are tailored to cause the organ of interest to uptake a proportionately larger amount of the material. Ideally, the radioisotope uptake of the organ of interest is very high and has limited or no overlap with other organs with strong uptakes. As the radiopharmaceuticals decay, they generate gamma radiation that is detected by a data acquisition sensor. In an embodiment, a gamma camera is used as the data acquisition sensor for planar imaging in 2-D, and for SPECT imaging in 3-D.

Figure 1:
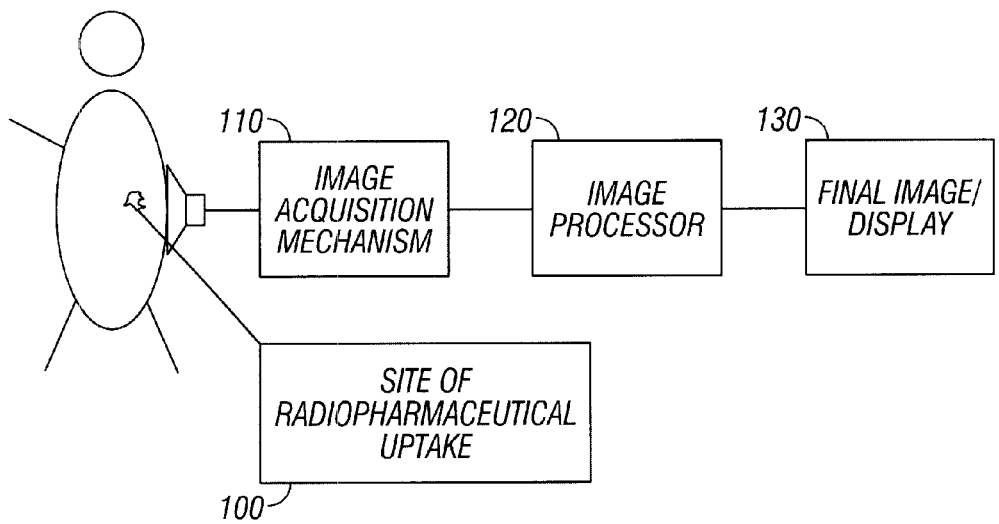
FIG. 1 shows a system imaging organ tissue using radiopharmacology.

FIG. 1 shows a system imaging organ tissue using radiopharmacology. The site of radiopharmaceutical uptake 100, has been located by the image acquisition mechanism 110 which then records the emission data from the organ tissue. The image processor 120 then receives the information from the image acquisition mechanism 110 and performs scatter correction. The scatter corrected information is then is passed to the system output interface 130.

Figure 2:
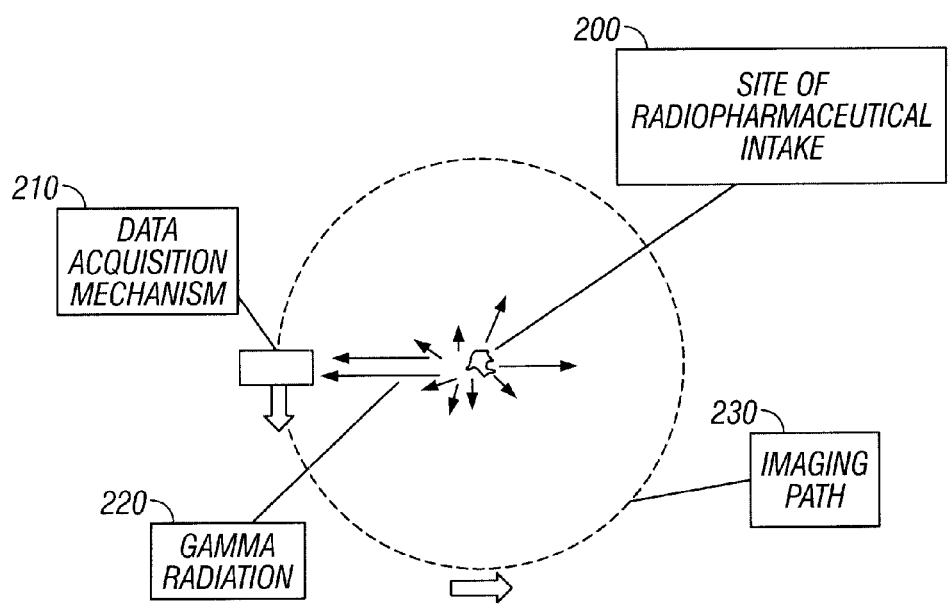
FIG. 2 shows how the camera may traverse 360 degrees in acquiring the images.

In an embodiment, images are taken at multiple projection angles. The camera may traverse 360 degrees in acquiring the images, as shown in FIG. 2. In certain embodiments, multiple cameras may be used to take images at different angles simultaneously. In one of the embodiments, the data acquisition mechanism 210 is a gamma camera. Preferably, the organ of interest is at the center of camera rotation 230 to facilitate obtaining information, such as the distance from the organ of interest to the detecting plane on the detector.

Figure 3:
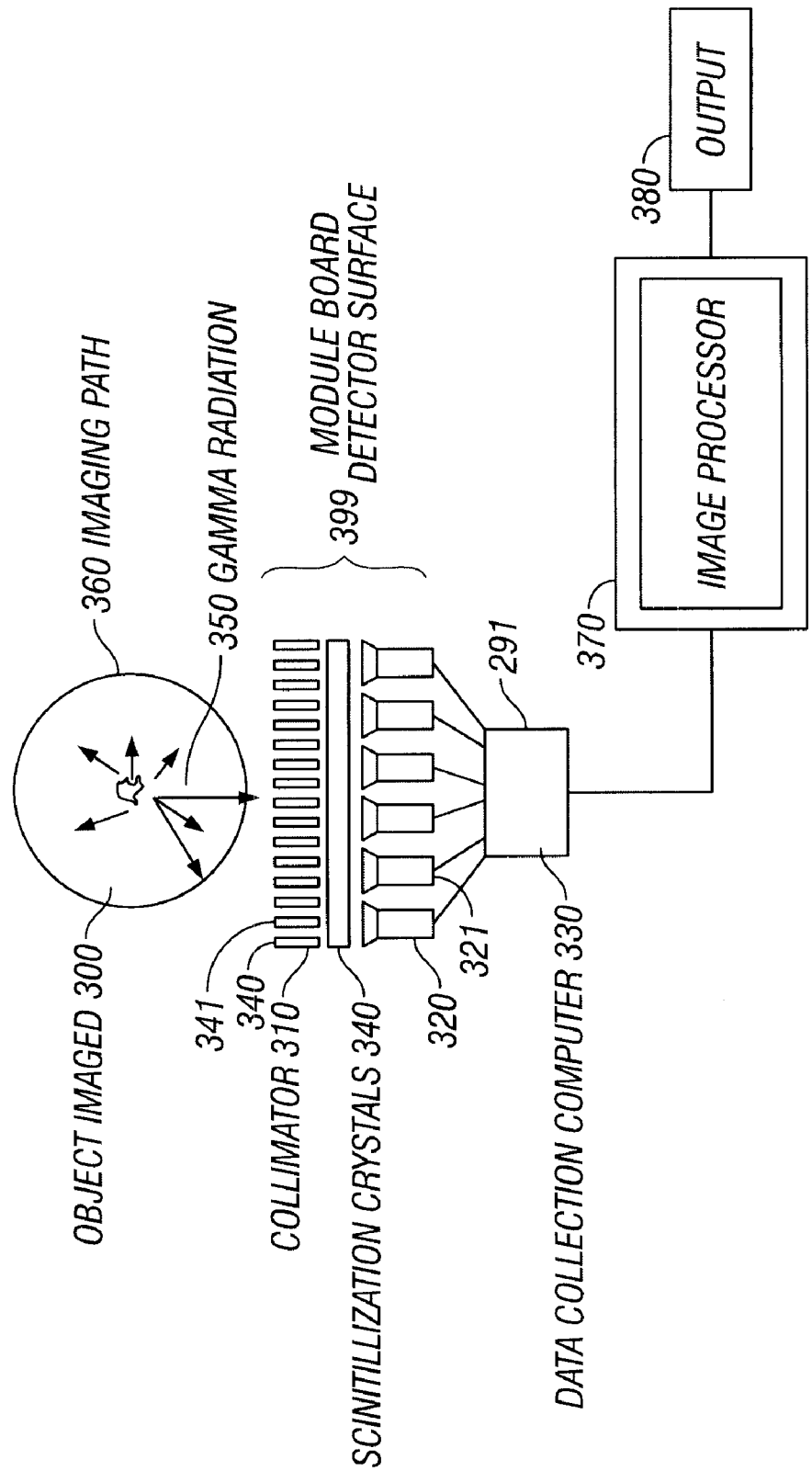
FIG. 3 shows the cross-section of a typical gamma camera.

FIG. 3 shows the cross-section of a typical gamma camera using a parallel hole collimator, a sheet scintillation crystal and photomultiplier tubes as the detector system.

Other types of gamma cameras may have detector systems that use other types of collimators, or segmented scintillators, or solid-state photodetectors or even devices that directly convert the gamma ray energy into an electrical signal without the use of a scintillator. Regardless of the method of conversion, the resulting signal is sent to the image processor 370.

Figure 4:
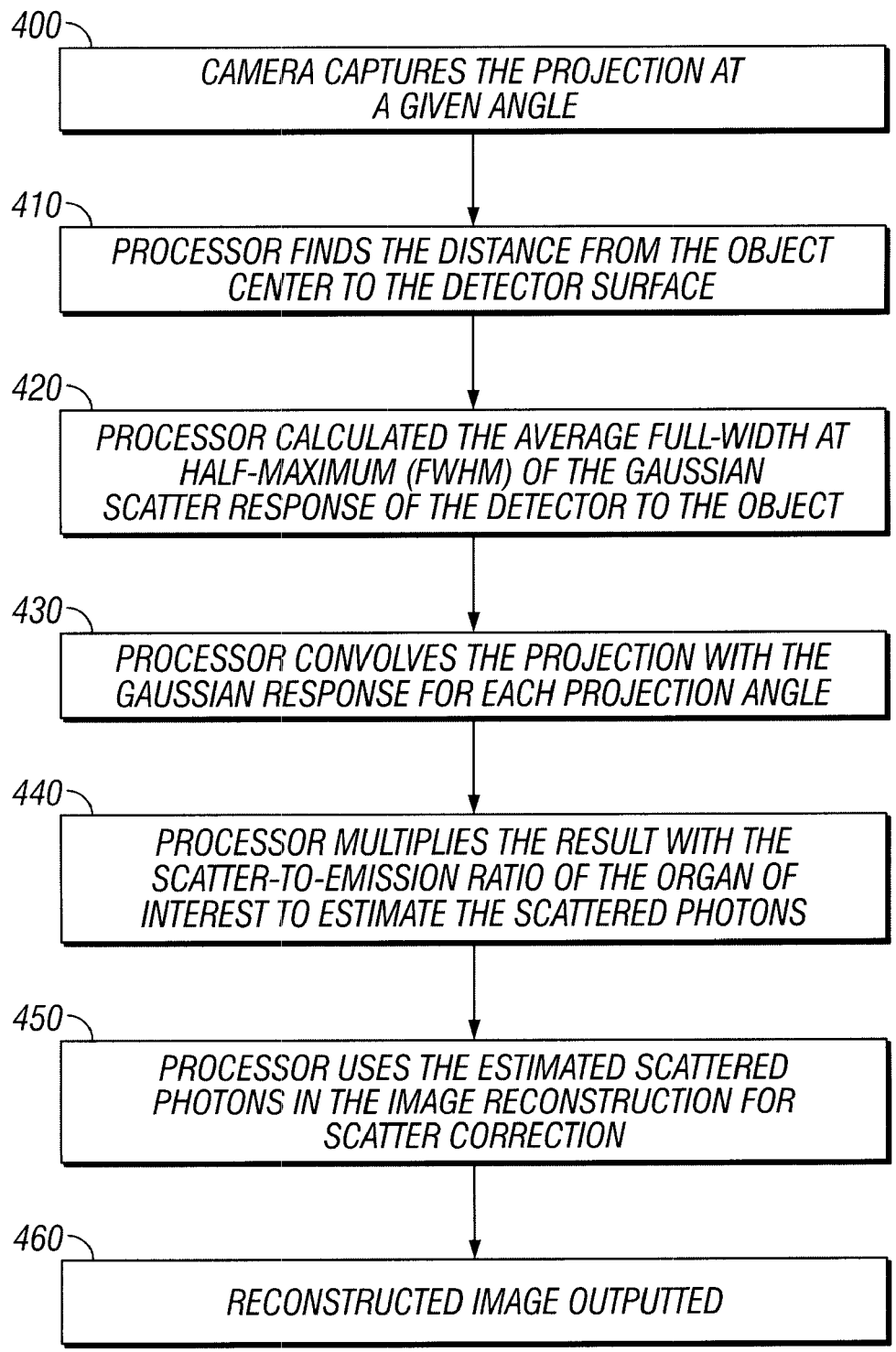
FIG. 4 shows a flowchart of the data acquisition and image processing data flow.

The image processor 370 carries out image correction, including scatter correction. FIG. 4 shows a flowchart of the scatter correction.

400 includes acquiring emissions data regarding the gamma radiation of the organ of interest. Scatter correction is performed on the data 410-450 by estimating its scatter. Finally, 460 the reconstructed image is outputted.

At each projection angle, 410 operates to cause the processor to find the average distance from the organ of interest to the detector surface. This can be done in several ways. In one embodiment, the radiation is modeled as a function of position and intensity. A threshold intensity is set, and all points above that threshold approximate the organ of interest. Then, the center is then calculated by approximating the shape as a geometric figure, such as an ellipse, circle, or trapezoid. In another embodiment, the emissions collected are modeled as a two-dimensional Gaussian function. The mean, or center, of the Gaussian is approximated as the point source of gamma radiation. The approximation is most accurate when the organ of interest is not truncated in the image-capture process. However, a 10-20% truncation of the actual organ may still yield accurate results.

Figure 5:
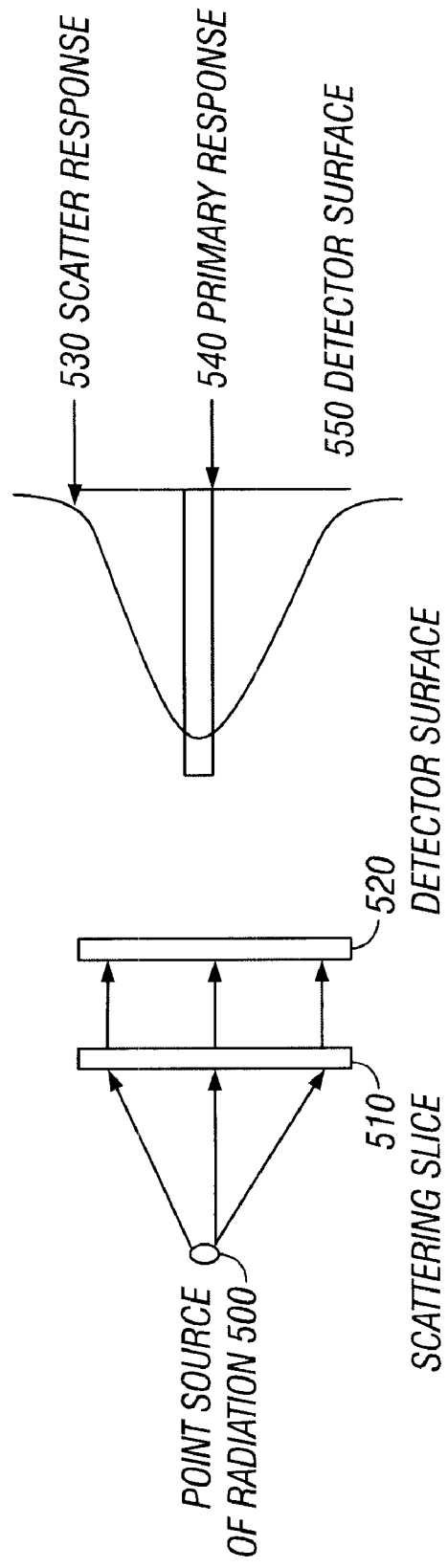
FIG. 5 shows the scatter response of a point source.
Figure 6:
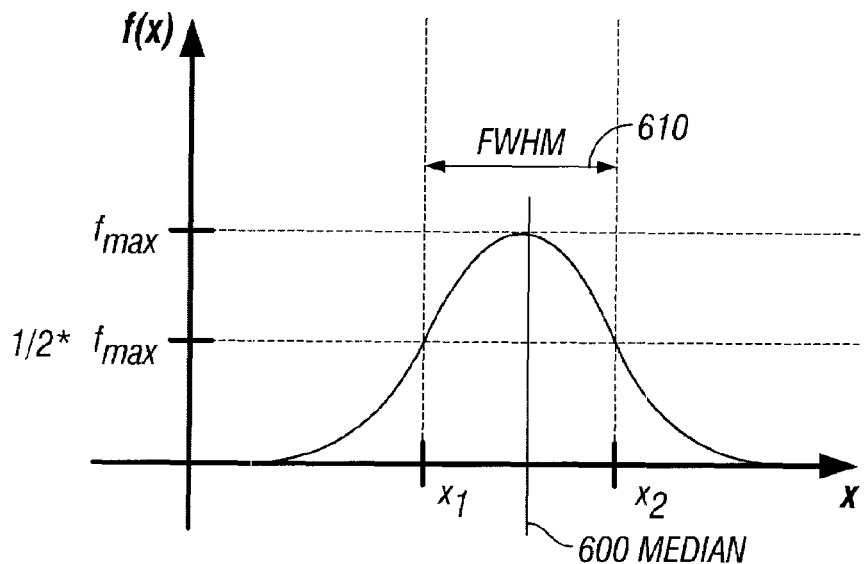
FIG. 6 shows the full-width-at-half-maximum of a Gaussian function.

After obtaining the average distance from the organ of interest to the detector surface at 410, the processor models the scatter response to a Gaussian function at 420. This assumes that the point source's scatter response to a scattering plane is a Gaussian function when the detector plane is parallel to the scattering plane. The Gaussian is shown as 530 in FIG. 5. The spread of the Gaussian function can be obtained using the model in Bai, et al., "A slice-by-slice blurring model and kernel evaluation using the Klein-Nishina formula for 3D scatter compensation in parallel and converging beam SPECT", May 2000, Phys. Med. Biol., Vol. 45, pps. 1275-1307 (Bai's PMI paper), the contents of which are herewith incorporated by reference, using the Full-Width-at-Half-Maximum (FWHM) metric 610, as illustrated in FIG. 6. The FWHM 610 indicates the likelihood that data points will be found close to the median. For example, the primary response 540 shown in FIG. 5 has a very tight Gaussian function, or a correspondingly small FWHM. Because of the intensity of the primary response, incident photons are less likely to be found far away from the median. By contrast, the scatter response 530 shown in FIG. 5 has a wider FWHM, indicating that photons may be found farther away from the median, as compared with the primary response.

According to Bai's PMI paper, the FWHM of the point source scatter response is directly proportional to the point source's distance to the scattering plane. The FWHM can be calculated if the distance from the point source to the scattering plane is prior knowledge. Then, the properties of the Gaussian can be known, as the FWHM is directly proportional to the standard deviation of the Gaussian according to the relationship, $$FWHM = 2\sqrt{2\ln(2)}\sigma \sim 2.35\,\sigma,$$

where $\sigma$ is the standard deviation of the Gaussian.

Figure 7:
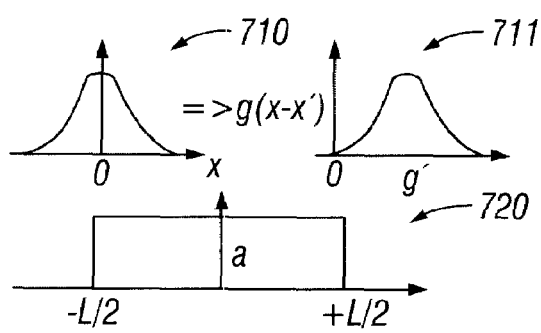
FIG. 7 shows an example of convolution.
Figure 7:
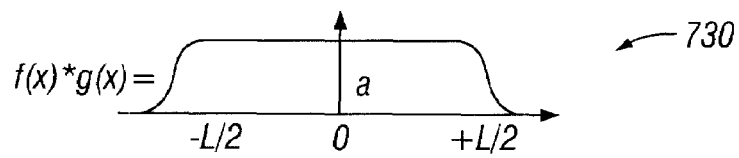

At 430, the processor convolves the Gaussian point source scatter response with the emission data. FIG. 7 shows an example of convolution. The operation is defined in 700. A Gaussian function 710 is convolved with a "rect" function, as defined at 720. The Gaussian is flipped on its axis 711, then integrated over the other function, 720. The resulting function is a combination of the two signals, as shown in 730. The convolution is analogous to "smearing" one signal (720) with the other signal (710). In the embodiment, the convolution weighs the emission data according to the probability that its recorded location was deflected by scatter as reflected by the Gaussian distribution function. Photons that are captured further away from the center of the organ of interest are given proportionately less intensity in the reconstructed image because of the likelihood that its location is affected by scatter.

After convolving the emission data with the Gaussian response, the resulting data is multiplied by the scatter-to-emission ratio of the organ of interest at 440, to estimate the photon scatter 450. The ratio reflects the percentage of the detected scattered photons to the total detected emission photons at each projection angle. The scatter-to-emission ratio can be obtained by phantom studies or from knowledge sets of a large patient database.

At 450, the estimated scatter photons can be used in the image reconstruction algorithms for scatter correction. For example, the scattered photons can be incorporated into the projector an iterative reconstruction algorithm for scatter correction, or they can be subtracted from the acquired emission data to form the scattered corrected data, the latter can then be used in a filtered-back-projection algorithm for image reconstruction.

The display receives data from the processor and translates the signal to an image which can be printed or viewed on a computer 460.

The general structure and techniques, and more specific embodiments which can be used to effect different ways of carrying out the more general goals, are described herein.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, this may be used in other forms of medical imaging, and with other kinds of hardware.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The computer may be a Pentium class computer, running Windows XP or Linux, or may be a Macintosh computer. The computer may also be a handheld computer, such as a PDA, cellphone, or laptop.

The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

What is claimed is:

1. An apparatus comprising:
    a data acquisition mechanism that acquires images from plural different angles and produces outputs indicative thereof;
    an image processing part, said image processing part operating to determine a first information related to measure of a Gaussian in at least multiple of said outputs, and to convolve said outputs with said first information to create corrected image data, wherein said first information is processed to correct for scatter in the image and represents scatter corrected values; and
    an output device which displays a corrected image formed from said corrected image data, and has been corrected for image scatter,
    wherein said image processing part convolves an approximated Gaussian scatter response of a point source representing said organ of interest.

2. An apparatus as in claim 1, wherein the image processing part further weights the corrected image by a previously known scatter-to-emission ratio specific to the organ of interest.

3. The apparatus of claim 1, wherein said data acquisition mechanism detects radioisotopes to indicate the organ of interest.

4. The apparatus as in claim 1, wherein said data acquisition mechanism includes a gamma camera.

5. The apparatus as in claim 1, wherein said output device includes a display screen.

6. A method comprising:
    obtaining medical images representing an organ of interest from plural different angles;
    processing information indicative of the medical images to correct for scatter in the medical images by approximating a Gaussian scatter response at each of said angles by approximating said organ of interest as a point source; and
    forming corrected information indicative of the medical images, and analyzing said corrected information, wherein said processing information comprises approximating all the points in the organ of interest are at an average distance from the detector surface and determining information about the image based on said approximating.

7. A method as in claim 6, wherein said determining information comprises determining a Gaussian scatter response of the organ of interest based on said approximating.

8. A method as in claim 6, wherein said determining information comprises convolving an approximated Gaussian scatter response of the organ of interest with the acquired emission data.

9. A method as in claim 8, further comprising further weighting the data using a scatter-to-emission ratio specific to the organ of interest at each projection angle.

10. A method as in claim 6, wherein said obtaining medical images comprises using a gamma camera to obtain medical images based on a radiopharmaceutical.

11. A method comprising:
    using a gamma camera to obtain medical images based on a radiopharmaceutical to obtain medical images representing an organ of interest from plural different projection angles;
    processing information indicative of the multiple medical images to correct for scatter in the medical images by determining an average distance between said organ of interest, and determining a Gaussian point scatter response at each of said angles, said processing information comprises approximating multiple different points in the organ of interest that are at an average distance from the detector surface and determining information about the image based on said determining and said approximating, to carry out a first scatter correction based on said point scatter response and said distance;
    weighting the information using a scatter-to-emission ratio specific to the organ of interest at each projection angle; and
    forming corrected information indicative of the medical images, based on both said first scatter correction, and on said weighting information.

12. A method as in claim 11, wherein said scatter correction comprises involving an approximated Gaussian scatter response of the point source with said information.

* * * * *